United States Patent [19]
Heindl et al.

[11] Patent Number: 6,057,120
[45] Date of Patent: May 2, 2000

[54] REDOX-ACTIVE COMPOUNDS AND THEIR USE

[75] Inventors: Dieter Heindl, Tutzing; Rupert Herrmann, Weilheim; Joachim Hönes, Zwingenberg; Hans-Peter Josel, Weilheim; Martina Junius-Comer, Tutzing; Hartmut Merdes, Heidelberg; Axel Schmidt; Ernst Selbertinger, both of München, all of Germany

[73] Assignee: Roche Diagnostics GmbH, Mannheim, Germany

[21] Appl. No.: 08/934,784

[22] Filed: Sep. 22, 1997

[30] Foreign Application Priority Data

Sep. 24, 1996 [DE] Germany ............ 196 39 169

[51] Int. Cl.[7] .............. C12Q 1/26; C12Q 1/00; G01N 33/53
[52] U.S. Cl. ............... 435/25; 435/4; 435/968; 568/30; 568/23; 568/74; 568/75; 568/76; 568/77; 544/3; 544/224; 544/353; 544/347
[58] Field of Search .................. 435/25, 4, 968; 568/30, 23, 74, 75, 76, 77; 544/3, 224, 353, 347

[56] References Cited

FOREIGN PATENT DOCUMENTS

| | | |
|---|---|---|
| 0 457 721A1 | 11/1991 | European Pat. Off. |
| 2 016 365 | 4/1970 | Germany . |
| 26 40 695 | 3/1978 | Germany . |
| 8-245596 | 9/1996 | Japan . |

OTHER PUBLICATIONS

Shetty et al., *Indian J. Chem.* vol. 4, Aug. 1966, "Redox Behaviour of Some Vat Dyes at Dropping Mercury Electrode".

Clarke, *J. Chem. Soc.*, 1967, (10) pp. 936–942, "Chemistry of Indanthrone. Part XIII. The Constitution of Indanthren B."

Chemical Abstracts, vol. 93, No. 15, 1980, Abstracts No. 150211d Synthesis of naphtol'2,3–a!phenazine derivatives.

López et al., *Tetrahedron Lett.*, vol. 37, No. 31. pp. 5437–5440, 1996, "Synthesis of a New Phenanthroline Derived Ligand with Acceptor Properties".

Streitweiser et al., 1976, "Introduction ot organic chemistry", No. XP002052085.

Arounaguiri et al, *Proc. Indian Acad, Sci.*, vol. 109, No. 2, Apr. 1997, pp. 155–158, "Redox–activated luminescence and light–induced nuclease activity of a new mixed–ligand ruthenium (II) complex".

Dikalov et al., *Biochemistry*, 1992, 31, pp. 8947–8953, "Role of Quinone–Iron (III) Interaction in NADPH–Dependent EnZymatic Generation of Hydroxyl Radicals".

*Primary Examiner*—Louise N. Leary
*Attorney, Agent, or Firm*—Nikaido Marmelstein Murray & Oram, LLP.

[57] ABSTRACT

The invention concerns the use of redox-active compounds for the production of detection reagents for a method for the determination of an analyte as well as reagent kits that contain these redox-active compounds. In addition new redox-active compounds are disclosed.

40 Claims, 11 Drawing Sheets

FIG. 1
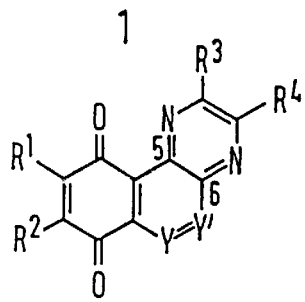
1
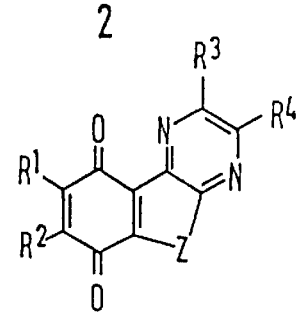
2
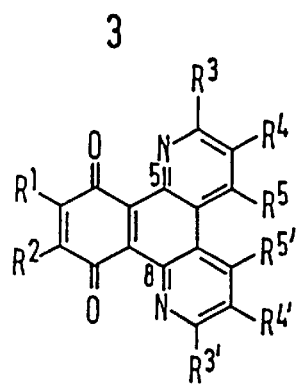
3
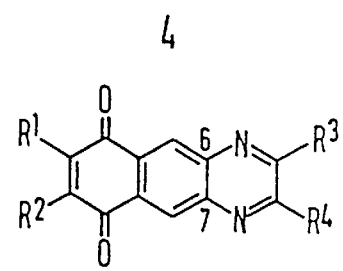
4
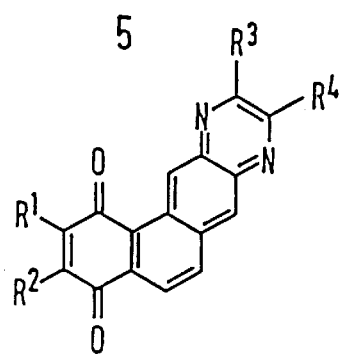
5
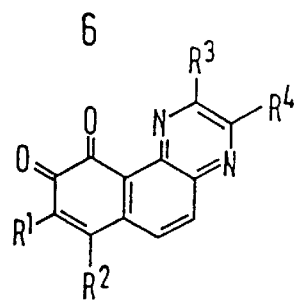
6
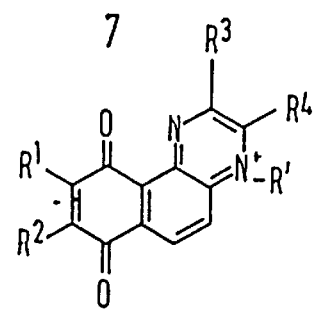
7
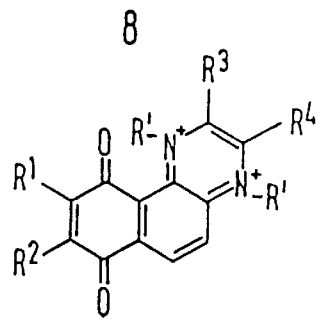
8

FIG. 3

| Indicator | UV/Vis oxidized form [nm] 0.1 m phosphate buffer pH=7 | UV/Vis reduced form [nm] 0.1 m phosphate buffer pH=7 |
|---|---|---|
| [2,3-h]/[2,3-j]isomer mixture [a] | 431 | 559 |
| [2,3-h]/[2,3-j]isomer mixture [a,b] | 417 nm | 650<br>689<br>785 (weak) |
| [2,3-h]/[2,3-j]isomer mixture [a] | 434 | 485<br>755 (weak)<br>850 (v. weak) |
| | 430 | 554<br>745 (weak)<br>830 (v. weak) |
| allocation unsure [c] | 425 | 529<br>730 (weak)<br>830 (v. weak) |
| or [2,1-b]isomer [d] | 450 (shoulder) | 510<br>600 (weak) | a) The isomers were not separated. In the table only the formula for the [2,3-h]isomer is stated.
b) 1,2-diamino-3-chloroanthraquinone was prepared according to: Gorelik M.V., Puckova V.v., J. Org. Chem. USSR (engl. transl.) 1869, 5, 361
c) Both isomers were isolated separately
d) One isomer was isolated. In the table only the formula for the [1,2-b]-isomer is stated.

REDOX-ACTIVE COMPOUNDS AND THEIR USE

DESCRIPTION

The invention concerns the use of redox-active compounds for the production of detection reagents for a method for the determination of an analyte as well as reagent kits which contain these redox-active compounds. In addition new redox-active compounds are disclosed.

Redox reactions enable analytes to be detected and determined in various sample materials. In these reactions an oxidizing or reducing system acts directly or via a mediator upon a redox indicator. The presence of the analyte leads to a reduction or oxidation of the redox indicator. If suitable redox indicators are used in which reduction or oxidation results in a detectable change of the molecular properties, it is possible to carry out a qualitative and/or quantitative detection of the analyte to be determined.

An analyte can for example be determined by a calorimetric detection method in which the colour of the detection reagent is changed by oxidation or reduction or by an electrochemical detection method. Examples of calorimetric detection reagents are resazurins, heteropoly acids (EP-B-0 431 456), tetrazolium compounds (EP-B-0 574 769), nitrosoaromatic compounds (EP-A-0 620 283), RIND compounds i.e. compounds in which an intramolecular reaction occurs when they are reduced (cf. e.g. EP-A-0 190 750 and WO 86/04681). Examples of redoxactive compounds in electrochemical detection methods are nitrosoaromatics, phenazinium salts, potassium hexacyanoferrate and benzoquinone (cf. e.g. EP-A-0 441 222 and EP-A-0 505 494).

However, the calorimetric detection reagents known from the state of the art have several disadvantages. Thus tetrazolium salts have a pronounced light instability. Furthermore the salt structure is destroyed by reduction and the resulting formazans are usually insoluble in water (H.-J. Guder, Indigo/Tetrazolium Dyes, chapter 12.1 in: Non radioactive labeling and detection of biomolecules, C. Kessler, pub., Springer-Verlag Berlin Heidelberg 1992). In the case of resazurins the colour difference between the oxidized and reduced form is too small for some applications. Due to an inadequate absorbance and an unfavourable absorption wavelength of the reduced form heteropoly acids have an inadequate sensitivity for many applications and, moreover, are less variable with regard to the absorption wavelength of the reduced form. RIND compounds are often too inert for diagnostic tests. On the other hand nitrosoaromatics are very susceptible to interference and the dye that is formed can fade as a result of over-reduction.

Hence the object of the present invention was to provide new redox-active compounds as detection reagents for the determination of analytes in which the disadvantages of the state of the art are at least partially eliminated. The new redox-active compounds should, on the one hand, be very variable with regard to their detectable molecular properties and, on the other hand, be adequately stable in their reduced as well as in their oxidized form.

This object is achieved according to the invention by using a new redox pair which has previously not been used in biochemical analytics or medical diagnostics which contains a benzoquinoxalinedione substructure or variants of this substructure such as e.g. a dehydroindanthrone or benzonaphthophenazinedione substructure. Dehydroindanthrenes are intermediates that have been known for a long time in the synthesis of anthraquinone dyes such as e.g. halogenated indanthrones. Several representatives of this class of substances are for example described in the monograph series "The Chemistry of Heterocyclic Compounds", vol. "Phenazines", G. A. Swan and D. G. I. Felton, 1975 Interscience Publishers Inc., New York, in particular pp. 431–433, 469 and 477. The synthesis of sulfonated derivatives is also known (cf. for example German Patent No. 129847 dated May 10, 1901 and the German Patent No. 216891 dated Dec. 13, 1908).

Compounds with a benzoquinoxaline substructure such as e.g. naphtho[2,3-a]phenazine-8,13-dione, benzo[a]-naphtho[2,3-h]phenazine-8,13-dione and variants with further condensed aryl residues and their chemical reduction to dyes have also been known for a long time (see "Phenazines", Supra).

Although redox pairs with a benzoquinoxalinedione substructure have now been known for almost 100 years, they have previously not been used in medical diagnostics or biochemical analytics. It has surprisingly now been found that these substances are excellently suitable as detection reagents especially for calorimetric detection methods. Hence they have a high light stability in the reduced as well as in the oxidized state and moreover can be modified extensively with regard to properties such as solubility, position of the absorption maxima of the oxidized and reduced form, redox potential etc. by the specific introduction of substituents such as hydrophilic residues, electron donor or acceptor residues. This enables a broad area of application such as e.g. in a test strip or liquid test. Moreover they can also be used as mediators in calorimetric and electrochemical applications.

Hence a subject matter of the present invention is the use of compounds of the structural formulae I or/and II or salts thereof as detection reagents or for the production of detection reagents for a method for the determination of an analyte:

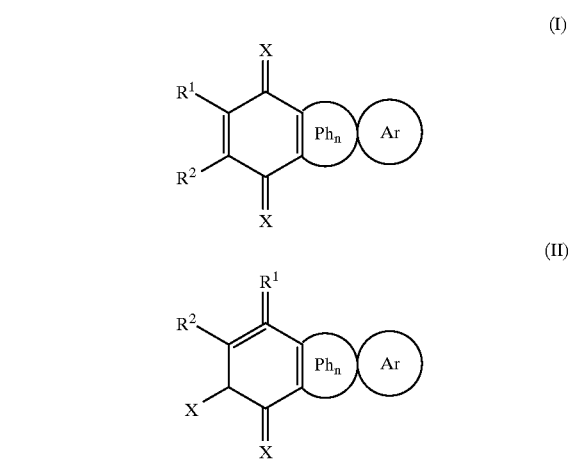

in which $R^1$ and $R^2$ each independently of one another are hydrogen, halogens or organic residues, X denotes O, S, C(Acc)$_2$, CH(Acc) or N(Acc) and Acc is an electron-attracting group, Ph denotes an optionally substituted phenyl ring, n is an integer from 0 to 4 and Ar denotes a group of the structural formulae IIIa, IIIb, IVa, IVb, Va, Vb, VIa or VIb:

(IIIa)
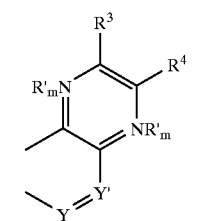

(IIIb)
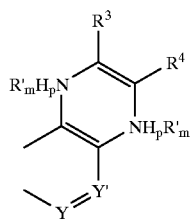

(IVa)
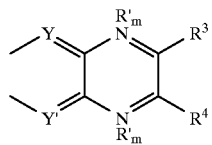

(IVb)
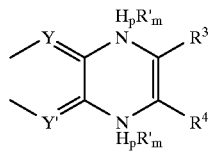

(Va)
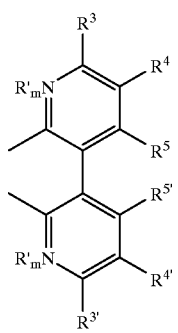

(Vb)
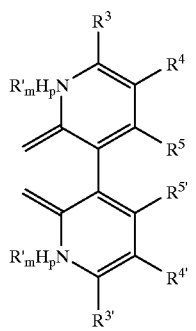

-continued (VIa)
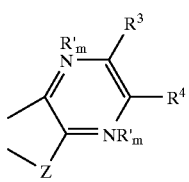

(VIb)
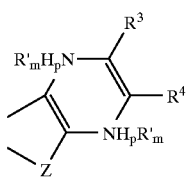

in which $R^3$, $R^{3'}$, $R^4$, $R^{4'}$, $R^5$ and $R^{5'}$ each independently of one another are hydrogen, halogen and organic residues, Y and Y' are each independently of one another N or $CR^6$, in which $R^6$ is hydrogen, halogen or an organic residue, Z is NR, O or S, in which R is an organic residue or hydrogen R' is in each case independently an optionally substituted alkyl or aryl residue and m is in each case independently 0 or 1 and if m equals 1, a nitrogen bound to R' in the structural formulae (IIIa), (IVa), (Va) and (VIa) carries a positive charge and an appropriate counterion is present and p equals 0 in the structural formulae (IIIb), (IVb), (Vb) and (VIb) and if m equals 0, p equals 1.

In addition to the compounds of the structural formulae I and II, it is also possible to use salts of these compounds e.g. acid addition salts. Examples of suitable counterions for such salts or for charged compounds with one or several residues R' are halogenides, $BF_4^-$, $PF_6^-$, $ClO_4^-$ or organic anions such as acetate. Charged compounds preferably contain only one residue R'.

In the compounds of the structural formulae I and II at least one of the residues $R^1$ and $R^2$ preferably comprises an aromatic or heteroaromatic ring system which can optionally carry substituents such as straight-chained, branched, saturated or unsaturated hydrocarbon residues that can optionally contain heteroatoms e.g. alkyl residues such as $C_1$–$C_4$ alkyl or haloalkyl residues, hydroxyalkyl residues such as $C_1$–$C_4$ hydroxyalkyl residues, halogen atoms e.g. F, Cl, Br, I or/and hydrophilic groups as defined in the following. Several substituents on the aromatic rings can also be bridged together e.g. via alkylene bridges. $R^1$ and $R^2$ can also be bridged together. $R^1$ and $R^2$ particularly preferably together form an aromatic or heteroaromatic ring system such as an optionally substituted benzene ring. In addition it is also possible that $R^1$ and $R^2$ together form a further $Ph_n$—Ar group.

The residue X in the formulae I and II is preferably O, $C(Acc)_2$, CH(Acc) or N(Acc). Acc is an electron-attracting substituent i.e. a substituent with a positive Hammett sigma value (cf e.g. Steric Effects in Organic Chemistry, John Wiley and Sons, Inc. 1956, pp. 570–574 and Progress in Physical Organic Chemistry, Vol. 2, Interscience Publishers, 1964, pp. 333–339). Specific examples of such substituents are cyano, carboxy, nitro, halogen, trihalogenmethyl, carbonyl, carbamoyl, sulfonyl, sulfamoyl, ester groups etc. Cyano, nitro and ester groups are preferred, cyano and nitro are especially preferred.

Ph denotes an optionally substituted phenyl ring in which the substituents can for example be halogen, alkyl or/and hydroxyalkyl (see above). n is preferably an integer from 0 to 1. If n equals 0, a compound of the structural formula I preferably has the skeletal structure that is shown for compounds 1 and 2 in FIG. 1. In this connection compound 1 can be interpreted as a naphthoquinone derivative in which two nitrogen atoms are located as substituents at positions 5 and 6 of the ring system. Compounds 3 and 4 in FIG. 1 represent variants of these structures. In this case the nitrogen atoms of the naphthoquinone ring system are at positions 5 and 8 (compound 3) or 6 and 7 (compound 4).

Compound 5 in FIG. 1 is a phenyl-like variant of compound 1 (n=1). A skeletal structure for a compound of the general structural formula II is compound 6 shown in FIG. 1.

Compounds 7 and 8 in FIG. 1 are once or twice alkylated variants of compound 1. The residue R' is an optionally substituted alkyl, preferably a $C_1$–$C_4$ alkyl residue and particularly preferably a $C_1$–$C_2$ alkyl residue or an optionally substituted aryl residue preferably a phenyl residue.

The groups of structural formulae IIIa and IIIb, IVa and IVb, Va and Vb, VIa and VIb each represent the oxidized or reduced variant of a compound. In these groups at least one of the residues $R^3$, $R^4$ and—if present—$R^{3'}$, $R^{4'}$, $R^5$ and $R^{5'}$ comprises an aromatic or heteroaromatic ring system which can optionally be substituted like $R^1$ and $R^2$. In the groups of structural formulae IIIa, IIIb, IVa, IVb, VIa and VIb $R^3$ and $R^4$ can be bridged together. They preferably together form a ring system which has at least partially an aromatic or heteroaromatic structure. It is also preferable that one or several of the residues e.g. $R^3$ and $R^4$ individually contain an aromatic and in particular a heteroaromatic ring system e.g. a pyridine ring.

In the groups of structural formulae Va and Vb (a) $R^3$ and $R^4$ or/and $R^{3'}$ and $R^{4'}$ or (b) $R^4$ and $R^5$ or/and $R^{4'}$ and $R^{5'}$ can each be bridged together. They preferably form a ring system which has at least partially an aromatic or heteroaromatic structure. The residues particularly preferably each together form an optionally substituted naphthalene or anthraquinone ring system. On the other hand one or several of the residues can also individually contain an aromatic or heteroaromatic ring system.

A major advantage of the compounds according to the invention is that the properties of individual compounds such as the spectrometric properties like the position of the absorption maxima, the electrochemical properties or the solubility properties can be widely varied by an almost arbitrary variation of the substituents. The compounds preferably contain one or several hydrophilic groups such as charge carriers to increase the water solubility which are preferably selected from (a) carboxylic acid, sulfonic acid and phosphonic acid groups as well as salts derived therefrom e.g. ammonium or alkali metal salts, (b) sulfuric acid monoester, phosphoric acid monoester and phosphoric acid diester groups as well as salts derived therefrom, (c) and primary, secondary or tertiary amine groups as well as quarternary ammonium groups in particular tertiary amine groups and quarternary ammonium groups. The hydrophilic groups may on the other hand also be non-ionic groups such as (d) polyhydroxy groups e.g. the residues of a polyvalent alcohol, a polyvalent amino alcohol e.g. Tris or a monosaccharide, oligosaccharide or polysaccharide and (e) $C_2$–$C_3$ polyalkyleneoxy or $C_2$–$C_3$ polyalkylenethio groups.

Sulfonic acid and amine groups are particularly preferred. Furthermore the hydrophilic groups can also contain a combination of two or more of the groups (a)–(e).

It is also possible to use the compounds of the structural formula (I) or/and (II) in the form of metal complexes. Examples of suitable metals are transition metals or rare earth metals.

The synthesis of the compounds according to the invention can be carried out according to known methods. Thus sulfonated dihydroindanthrones can be obtained by sulfonating indanthrenes and subsequent oxidation. The condensation of orthoquinones with ortho diaminoaryl compounds to form phenazines is a standard reaction (cf. G. A. Swan in The Chemistry of Heterocyclic Compounds: Phenazines, pubis. A. weissberger, Interscience Publisher Inc., New York 1975). The synthesis of compounds in which Ar denotes a group of the structural formula (Va) or (Vb) by a Wittig reaction is described for example in a publication by Nicolaides and Litinas (J. Chem. Res. (M) 1983, 658–663).

The compounds according to the invention are used to produce detection reagents for methods for the qualitative or/and quantitative determination of an analyte. This determination can be carried out in aqueous liquids e.g. samples of body fluids such as blood, serum, plasma or urine, samples of aqueous waste or foods. The method can be carried out as a wet test e.g. in a cuvette or as a dry test on a corresponding reagent carrier.

Analytes can be determined by a single reaction or by a sequence of reactions. The determination of the analyte preferably comprises a redox reaction in which there is a detectable change of the molecular properties of the detection reagents according to the invention e.g. a change in the spectroscopic properties such as absorbance or fluorescence, or a change in the electrochemical properties.

It is particularly preferable to determine a change in absorption properties which can be achieved by spectroscopic detection methods in the IR, UV and in particular in the visible range. It was surprisingly found that the introduction of hydrophilic groups such as sulfonic acid groups resulted in an absorption maximum of the reduced form of the compounds according to the invention in the long wavelength range of about 600 to 800 nm so that no interference by serum components occurs when determining analytes in serum. This applies especially to groups of the structural formula (III) in which $R^3$ and $R^4$ together form a naphthalene ring system and the hydrophilic groups e.g. sulfonic acid groups are bound to a C atom which is in the direct vicinity of a pyrazine nitrogen.

In addition to spectrometric properties it is also possible to determine the electrochemical properties of the detection reagents e.g. changes in the redox potential or in the current. Examples of suitable electrochemical detection methods are cyclovoltammetry and amperometry.

The analytes which are determined by the detection reagents according to the invention can for example be cells e.g. bacteria, yeasts, fungi, plant cells or animal cells such as leukocytes in which case in particular reducing or oxidizing activities of these cells can be detected. Furthermore enzymes can be detected as analytes e.g. oxidoreductases such as oxidases e.g. peroxidase or dehydrogenases e.g. glucose oxidase, lactate dehydrogenase, or hydrolases e.g. lipase, galactosidase, alkaline phosphatase etc., biological or chemical substances which can participate in a redox reaction with the detection reagents e.g. ascorbic acid, cysteine, glutathione, thioredoxin, etc., metabolizable substances e.g. glucose, lactic acid, triglycerides, cholesterol etc., immunologically reactive substances e.g. antigens, haptens and antibodies and nucleic acids or nucleic acid derivatives such as peptidic nucleic acids.

Consequently the compounds according to the invention can be used as detection reagents in numerous fields of application e.g. in liquid or dry tests for clinical diagnostics. Furthermore they can be used in histology to detect and locate reducing or oxidizing enzymes, in cell biology for cell proliferation and cytotoxicity tests and additionally for germination tests of seeds, for vital staining, for the histochemical and cytochemical detection of dehydrogenases in tissue e.g. in normal or tumour tissue and as detection agents in thin layer chromatography e.g. to detect corticosteroids.

The compounds of the general structural formulae I and II can also be used as direct detection reagents i.e. the analyte is determined directly via a detectable change of the molecular properties of the compounds. On the other hand the compounds can also act as mediators and can be used coupled to a further detection system i.e. the analyte is not determined directly via a change in the molecular properties of the compounds but rather via a further detection system e.g. an electrochemical detection system (cf. e.g. EP-A-0 441 222) or other chemical compounds e.g. tetrazolium compounds.

In a preferred embodiment of the present invention the compounds according to the structural formulae I and II are used to detect an oxidoreductase activity in which the analyte to be determined is on the one hand the oxidoreductase itself or, on the other hand, it can be an oxidoreductase substrate. The detection is preferably carried out in the presence of an oxidoreductase co-substrate in particular the system $NAD(P)^+$ or $NAD(P)H/H^+$ or even other cosubstrates such as flavines or PQQ.

The oxidoreductase activity can be determined in the presence of mediators which catalyse the transfer of electrons from the enzyme cosubstrate onto the oxidized compound or the converse reaction i.e. the transfer of electrons from the reduced compound onto the enzyme co-substrate. Examples of suitable mediators for NAD(P)-dependent dehydrogenases are the enzyme diaphorase or N-methylphenazinium methosulfate. However, it is also possible to directly transfer electrons from an enzyme cosubstrate onto the oxidized compound or to directly transfer electrons from the reduced compound onto an enzyme cosubstrate.

A further preferred embodiment of the present invention is the use of compounds of the structural formulae I or/and II to detect a dye-oxidoreductase activity e.g. a glucose dye-oxidoreductase activity. In this case the enzymes can be transferred directly from an enzyme substrate onto the oxidized compound. However, it is preferable to use a coenzyme mediator e.g. PQQ. For the determination of other analytes, an oxidizing activity can also be detected using the reduced form of the compound according to the invention.

Yet a further preferred embodiment of the invention is the use of compounds of the structural formulae I or/and II to detect a hydrolase activity in which the hydrolase or a hydrolase substrate can be the analyte to be determined. Such a detection is preferably carried out via an oxidative coupling system e.g. by a β-galactosidase coupling in which the hydrolysis leads to the formation of an oxidizable compound by cleavage of a hydrolase substrate which when oxidized reduces the oxidized compound according to the invention.

In addition the present invention concerns a method for the determination of an analyte in a sample which is characterized in that the sample is contacted with a reagent which contains at least one compound of the structural formulae I or/and II and the analyte is determined via a change in the detectable properties of the reagent. A reagent according to the invention for the determination of an analyte contains at least one compound of the structural formulae I or/and II and can be present as a component of a reagent kit which additionally contains other test components such as mediators, accompanying substances such as buffers, salts, detergents and optionally other auxiliary reagents in the form of a reagent or of several separate partial reagents. The accompanying substances can optionally be selected such that they enable a modification of the molecular properties such as of the spectral characteristics of the compounds according to the invention e.g. by pH change or/and by addition of detergents.

The reagent according to the invention can be a reagent for a liquid test which for example is present in the form of a solution or suspension in an aqueous or non-aqueous liquid or as a powder or lyophilisate. On the other hand the reagent can also be present as a dry test reagent e.g. absorbed into an absorptive or swellable carrier or incorporated into a light-sensitive film layer. A liquid test reagent preferably contains all components required for the method according to the invention. Water and mixtures containing water soluble organic solvents such as alcohols, acetone or dimethylformamide come into consideration as solvents or suspending agents. For stability reasons it may be advantageous to distribute the components required for the test into two or several partial reagents which are not mixed until the actual analysis.

The reagent according to the invention can also be present in the form of a test strip. Such test strips are known in various embodiments cf. e.g. DE-A-32 47 608, EP-A-0 262 445 or EP-A-0 256 806. In a test strip the components of the reagent required to carry out the method of determination are present on solid carrier layers. Absorptive or/and swellable materials come into consideration as carrier layers which are wetted by the sample liquid to be examined. Examples are gelatin, cellulose, organic polymers and copolymers or synthetic fibre fleeces. The components of the reagent are present in a solid form in or on these carrier materials. When the sample is applied to the test strip or the test strip is immersed in the sample a liquid environment forms in the strip within which the detection reaction progresses. A colour change caused by the reaction can be evaluated visually or photometrically e.g. by reflectometry or also electrochemically.

The compounds according to the invention can in addition also be incorporated into light-sensitive film or photo layers. In this case the carrier material is an at least essentially transparent film material which is preferably transparent to electromagnetic radiation of wavelengths of 200–900 nm. Suitable carrier materials are organic polymers and copolymers e.g. polystyrenes, polyesters, polycarbonates, cellulose esters etc. or copolymers thereof (cf. e.g. WO86/04681, examples 11–13).

The concentration of the compounds that are used depends on the concentration of the analyte to be measured. Typical concentrations for the analytes to be measured in the method according to the invention are $10^{-6}$ to $10^{-1}$ mol/l in the case of substrates or down to $10^{-15}$ mol/l when detecting enzyme activities. Correspondingly typical concentrations of the compounds used are $10^{-6}$ to 1 mol/l. If further detectable compounds e.g. tetrazolium compounds or certain oxidative coupling reagents are used in combination with the compounds according to the invention, these are preferably in at least a stoichiometric ratio to the compounds according to the invention particularly preferably in a 1.5 to 2-fold excess.

A further subject matter of the present invention are new compounds of the general structural formulae I and II in particular those compounds which contain at least one hydrophilic group as defined above except for indanthrene monosulfonic acid, indanthrene disulfonic acid and sodium and potassium salts thereof.

New compounds with the general structural formulae VIIa, VIIb, VIIIa or VIIIb are particularly preferred:

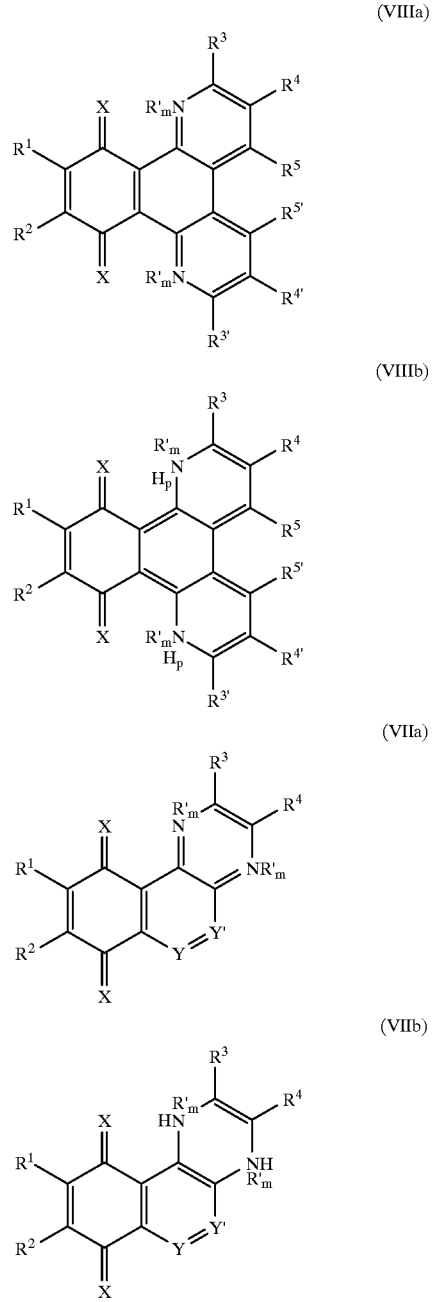

in which $R^1$, $R_2$, X, R', m, p, $R^3$, $R^4$, $R^5$, $R^{3'}$, $R^{4'}$, $R^{5'}$, Y and Y' are defined as in the compounds (I). X particularly preferably denotes O. In addition it is preferred that at least one of the residues $R^1$ and $R^2$ or/and $R^3$, $R^4$, $R^5$, $R^{3'}$, $R^{4'}$, $R^{5'}$ comprises an aromatic or heteroaromatic ring system. $R^1$ and $R^2$ can for example form an optionally substituted benzene ring and in the compounds (VIIa) and (VIb) $R^3$ and $R^4$ can be bridged to one another and can for example form an optionally substituted naphthalene or anthraquinone ring system.

Correspondingly in compounds (VIIIa) and (VIIIb) (a) $R^3$ and $R^4$ or/and $R^{3'}$ and $R^{4'}$ can be bridged together or (b) $R^4$ and $R^5$ or/and $R^{4'}$ and $R^{5'}$ can be bridged to one another and can for example form a ring system which contains an aromatic or heteroaromatic structure.

Y and Y' preferably in each case denote $CR^6$ where $R^6$ has the meanings given for the compound (I).

It is intended to elucidate the invention in more detail by the following figures and examples.

BRIEF DESCRIPTION OF THE DRAWINGS

FIG. 1 shows the general structural formulae for preferred indicator substances according to the invention FIG. 3 shows structural formulae of further benzonaphthophenazine-8,13 diones according to the invention.

EXAMPLES

Examples 1–4
Synthesis of benzonaphthophenazine-8,13-diones

The compounds according to examples 1–4 are synthesized by condensing diaminoanthraquinones with ortho dicarbonyl compounds.

Example 1

8,13-dihydro-benzo[a]naphtho[2,3-h]phenazine-8, 13-dione-3,6-disulfonic acid disodium salt and 10, 15-dihydro-benzo[a]naphtho[2,3-j]phenazine-10,15-dione-3,6-disulfonic acid disodium salt A suspension of 4.8 g (0.02 mol) 1,2-diaminoanthraquinone and 7.2 g (0.02 mol) 1,2-naphthoquinone-3, 6-disulfonic acid disodium salt (prepared according to W. Langenbeck, H. Le Blanc, B. Lukowcyk. Chem. Ber. 1954, 87, 496; C. Grundmann in "Methoden der Organischen Chemie (Houben Weyl) publ. C. Grundmann Georg Thieme Verlag Stuttgart 1979, vol. VII 3b (Chinone II) p. 64–75) in 100 ml acetic acid is boiled for 2 h under reflux while stirring. After cooling to room temperature it is admixed with 1000 ml water. The mixture is filtered and subsequently the filtrate is extracted by shaking three times with ethyl acetate. The separated aqueous phase is concentrated to 50 ml. After column chromatography on LH 20 using water as the eluant, 1 g of the two isomers is obtained.
(Data for one isomer)

neg. LSIMS (water/gly/m-NBA): m/z 542 [m-Na+H], 519 [m-2Na+H], 520 [m-2Na+2H]

UV/Vis absorption (0.1 M phosphate buffer pH=7.0): 420 nm; after reduction with ascorbic acid: 780, 703, 570 nm 1H-NMR (d6-DMSO) ppm: 7.92 (t, [1H], 7.99 (t [1 H]), 8.18 (d, [1 H]), 8.20 (d, [1 H]), 8.32 (d, [1 H]), 8.35 (s, [1 H]), 8.58 (d, [1 H]), 8.76 (s, [1 H]), 8.78 (d, [1 H]), 9.35 (d, [1 H]), 13C-NMR (d6-DMSO) ppm: 125.53, 125.75, 126.06, 126.65, 126.69, 128.64, 130.98, 131.31, 131.58, 133.65, 133.75, 134.75, 135.51, 136.08, 137.98, 140.68, 141.55, 143.11, 143.44, 150.63, 182.35, 183.02
(Data for the other isomer)

neg. LSIMS (water/gly/m-NBA): 520, [m-2Na+2H],

1H-NMR (d6-DMSO) ppm: 7.95 (t,[1 H]), 7.08 (t,[1 H]), 8.17 (d,[1 H]), 8.19 (d,[1 H]), 8.32 (s,[1 H]), 8.36 (d [1 H]), 8.68 (d [1 H]), 8.73 (s, [1 H]), 8.73 (d, [1 H]), 9.40 (d, [1 H])

UV/Vis absorption (0.1 M phosphate buffer pH=7.0): 414 nm; after reduction with ascorbic acid: 805, 660, 555 nm.

Figure 2:
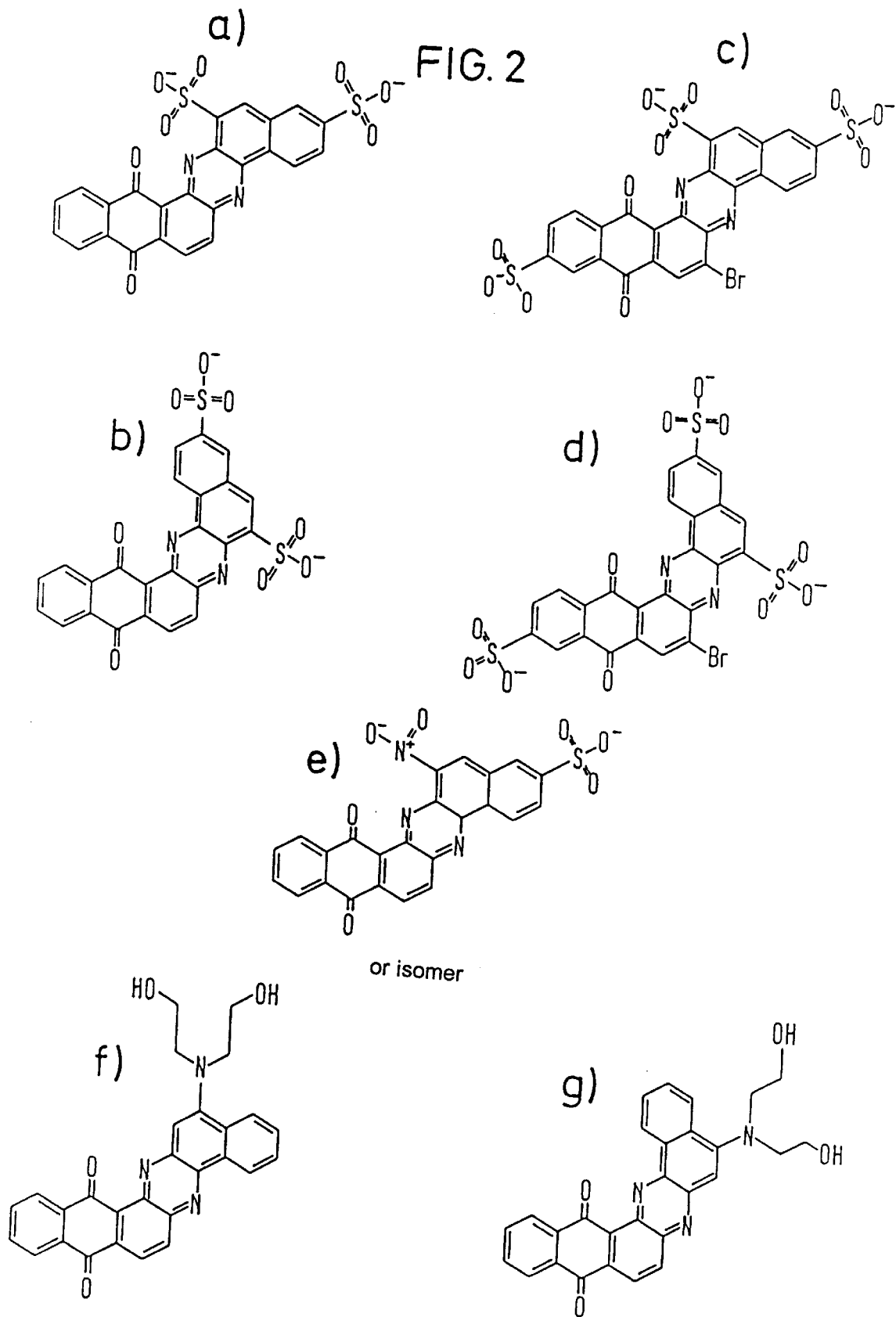
FIG. 2 shows structural formulae of the benzonaphthophenazine-8,13 diones synthesized in examples 1–4.

The structural formulae of the two isomers are shown in FIG. 2a and 2b.

Example 2

15-bromo-8,13-dihydro-benzo[a]naphtho[2,3-h] phenazine-8,13-dione-3,6,11-trisulfonic acid trisodium salt and 8-bromo-10,15-dihydro-benzo[a] naphtho[2,3-j]phenazine-10,15-dione-3,6,12-trisulfonic acid trisodium salt 0.6 ml (15 mmol) bromine is added to a solution of 1 g (3 mmol) 2-amino-anthraquinone-6-sulfonic acid (O. Bayer in "Methoden der Organischen Chemie (Houben Weyl) publ. O. Bayer Georg Thieme Verlag Stuttgart 1979, vol. VII 3 c (Chinone III) p. 182) in 5 ml 75% sulphuric acid. It is heated for 3 h to 105° C. and 50 ml water is added after cooling to room temperature. 1.5 g of the crude product (1,3-dibromo-2-amino-anthraquinone-6-sulfonic acid) is reacted without purification with 15 ml of a 25% ammonia solution in an autoclave at 100° C. The product (1,2-diamino-3-bromo-anthraquinone-6-sulfonic acid) is precipitated by addition of saturated sodium chloride solution and purified by column chromatography on LH 20 using methanol/water 1:1 as the eluant (the violet band is collected).

A suspension of 400 mg (1 mmol) 1,2-diamino-3-bromo-anthraquinone-6-sulfonic acid and 550 mg (1 mmol) 1,2-naphthoquinone-3,6-disulfonic acid disodium salt (see above) is boiled under reflux for 2 h in 6 ml acetic acid while stirring. The reaction mixture is processed similarly to example 1. 100 mg of each of the two isomers is obtained.
Data for one isomer neg. LSIMS (water/gly/m-NBA): m/z 677 [m-3Na+H], 678 [m-3Na+2H]

UV/Vis absorption (0.1 M phosphate buffer pH=7.0): 422 nm; after reduction with ascorbic acid: 802, 716, 660 nm
Data for the other isomer UV/Vis absorption (0.1 M phosphate buffer pH=7.0): 416 nm; after reduction with ascorbic acid: 810 (weak), 715 (weak), 545 nm.

The structural formulae of the two isomers are shown in FIG. 2c and d.

Example 3

8,13-dihydro-3-nitro-benzo[a]naphtho[2,3-h]-phenazine-8,13-dione-6-sulfonic acid or 10,15-dihydro-3-nitro-benzo[a]naphtho[2,3-j]phenazine-10,15-dione-3,6-sulfonic acid 6 mmol 5-amino-6-hydroxy-naphthalene-2 sulfonic acid (H. E. Fierz-David, L. Blangey, H. Kaul, Helv. Chim. Acta 1946, 29, 1765) is heated for 30 min to 80° C. in 10 ml 68% nitric acid. After cooling rapidly to 0° C. 50 ml saturated sodium chloride solution is added. The brown-green precipitate is suction filtered and air dried. The crude 3-nitronaphtho-1,2-quinone-6 sulfonic acid is boiled for 2 h under reflux with 3 mmol diamino-anthraquinone in 20 ml glacial acetic acid. It is processed as described in example 1. Yield: 40 mg (only one isomer isolated).

neg. LSIMS (water/gly/m-NBA): m/z 484 [m-Na],

UV/Vis absorption (0.1 M phosphate buffer pH=7.0): 410 nm; after reduction with ascorbic acid: 800 (weak), 638 nm.

The structural formula of the compounds is shown in FIG. 2e.

Example 4

8,13-dihydro-4-bis(2-hydroxyethyl)amino-benzo[a]-naphtho[2,3-h]phenazine-8,13-dione and 10,15-dihydro-4-bis(2-hydroxyethyl)amino-benzo[a] naphtho-[2,3-j]phenazine-10,15-dione 238 mg (1 mol) diaminoanthraquinone and 261 mg (1 mol) 4-Bis(2-hydroxyethyl)amino-1,2-naphthoquinone (synthesized from 1,2-naphthoquinone-4-sulfonic acid sodium salt and diethanolamine as specified in: C. Grundmann in "Methoden der Organischen Chemie (Houben Weyl) publ. C. Grundmann Georg Thieme Verlag Stuttgart 1979, vol. VII 3b (Chinone II) p. 64–75) are boiled for 2 h under reflux in 20 ml glacial acetic acid while stirring. After cooling to room temperature the acetic acid is removed by distillation in a vacuum. The residue is separated on silica gel using an ethyl acetate/methanol/glacial acetic acid mixture (2:2:1) as the eluant. The lemon-yellow band is collected. Yield: 20 mg (isomer mixture) UV/Vis absorption (H₂O): 445 nm; after reduction: 548 nm The structural formula of the two isomers are shown in FIG. 2f and 2g.

Further compounds that were obtained by the processes described above by condensing diamino-anthraquinones known in the literature or described in examples 1–4 with 1,2-dicarbonyl compounds that are known in the literature or are commercially available or hydrates thereof are summarized in FIG. 3.

Examples 5–6
Synthesis of dehydroindanthrene sulfonic acids

Dehydroindanthrone sulfonic acids are obtained by sulfonating indanthrenes and subsequently oxidizing them. The production processes are described in the Friedlander textbook.

Example 5:
Dehydroindanthrone monosulfonic acid (according to Lit.: Fr. IX, 783)

0.5 g (8 mmol) boric acid is dissolved in 10 ml concentrated sulfuric acid. 0.3 g (0.7 mmol) indanthrone is added to the hot solution and the mixture is boiled for 4 hours under reflux. The mixture is cooled and diluted with 50 ml distilled ice water. Subsequently it is filtered, removing most of the sulphuric acid. The residue is boiled in a small amount of distilled water, hot filtered, washed and dried (yield: 0.25 g indanthrone monosulfonic acid). It is then stirred for 15 min while cooling on ice with a mixture of 10 ml concentrated sulphuric acid and 10 ml fuming nitric acid. Subsequently it is diluted to 50 ml with water while cooling on ice and suction filtered. The brown solid is purified on Sephadex LH-20 using methanol as the eluant. The fractions which colour blue when ascorbic acid is added are pooled. The solvent is removed by distillation and the residue is taken up in water. The solution is lyophilized. Yield: 90 mg.

UV/Vis absorption: (0.1 M phosphate buffer pH=7.0): 392 nm; after reduction 717, 667 nm.

Figure 4:
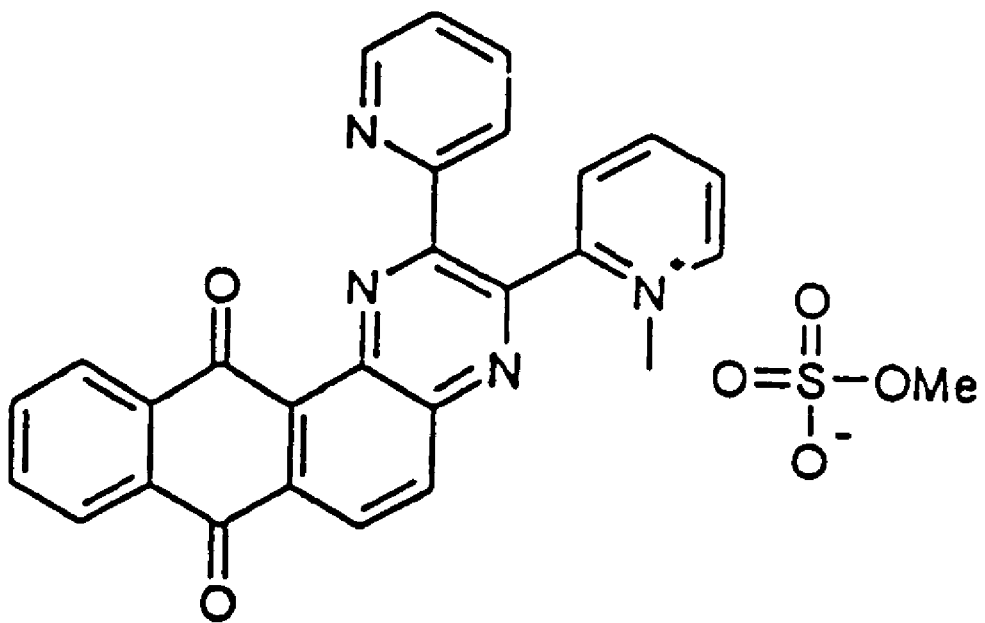
FIG. 4 shows structural formulae of the dehydroindanthrene sulfonic acids synthesized in examples 5 and 6 and of the pyridylnaphthoquinoxaline-7,12-dione-methylsulfate synthesized in example 7.

The structural formula of the compound is shown in FIG. 4 upper part (n=1).

Example 6:

Preparation of dehydroindanthrone sulfonic acid disodium salt (according to Lit.: Fr. VI, 413)

2 g indanthrone is heated to boiling with 1 g boric acid and 60 ml fuming sulphuric acid (oleum, 30% $SO_3$) until a sample of the reaction solution yields a clear blue solution when diluted with a large amount of water. Subsequently the oily solution is carefully added dropwise to 200 ml ice water. The mixture is suction filtered over a D 4 glass frit. A filter cake is obtained which still contains water and sulphuric acid. The indanthrone disulfonic acid from the above reaction which is still wet is stirred for 15 min with 20 ml fuming nitric acid while cooling on ice. Subsequently it is neutralized slowly with 50% sodium hydroxide solution while cooling. The solution is desalted over Diaion using water as the eluant. The brown eluate is concentrated and separated on Sephadex LH-20 using water as the eluant similarly to example 5. Yield. 200 mg.

UV/Vis absorption: in 0.1 M phosphate buffer pH=7.0: 394 nm; after reduction 790, 714, 655 (sh).

The structural formula of the compounds is shown in FIG. 4 upper part (n=2). The substitution positions of the sulfonic acid residues are presumably positions 7 and 16.

Example 7

2-(pyrid-2-yl)-3-(1-methylpyrid-2-ylium)naphtho-[2,3-a]quinoxaline-7,12-dione- methylsulfate 2.38 g (10 mmol) 1,2-diaminoanthraquinone and 2.12 g (10 mmol) bipyridiyl are boiled to reflux in 10 ml glacial acetic acid for 5 min while stirring. After cooling to room temperature it is suction filtered. The residue is recrystallized from glacial acetic acid. (Yield: 2.45 g 2,3-(dipyrid-2-yl)-naphtho[2,3-a] quinoxaline-7,12-dione). This residue (5.84 mmol) is heated for 30 min to 100° C. together with 0.6 ml (6.42 mmol) dimethylsulfate in 10 ml nitrobenzene. After cooling to room temperature it is precipitated by addition of 50 ml ether. The residue is suction filtered and re-precipitated four times from acetonitrile using ether. It is taken up in 200 ml boiling isopropanol and filtered. The filtrate is admixed with ether/petroleum ether 1:1. Fine pale-orange needles precipitate. Yield: 250 mg.

The structural formula of the compound is shown at the bottom of FIG. 4.

LSIMS: m/z 429

UV (0.1 M phosphate buffer pH=7.0): 380 nm after reduction with ascorbic acid: 533 nm;

1 H-NMR ($CD_3CN$) ppm: 3.51 (s, [3H]), 4.25 (s, [3H]), 7.46 (m, [1H]), 7.90 (m[3H]), 8.15 (dd,[2H], 8.24 [d, [1H]), 8.29 (dd, [2H]), 8.55 (dd, [2H]), 8.74 (d, [1H]), 8.83 (d, [1H]), 8.94 (d, [1H]).

13C-NMR ($CD_3CN$) ppm: 47.46, 53.65, 124.97, 126.52, 127.27, 127.62, 128.13, 128.65, 128.96, 129.99, 132.88, 134.90, 135.84, 136.11, 138.42, 139.08, 140.70, 143.39, 146.19, 146.67, 147.05, 149.80, 152.02, 153.77, 154.81, 157.83, 183.45, 183.85.

Example 8

Reaction of an indicator with glucose/glucDOR

Figure 5:
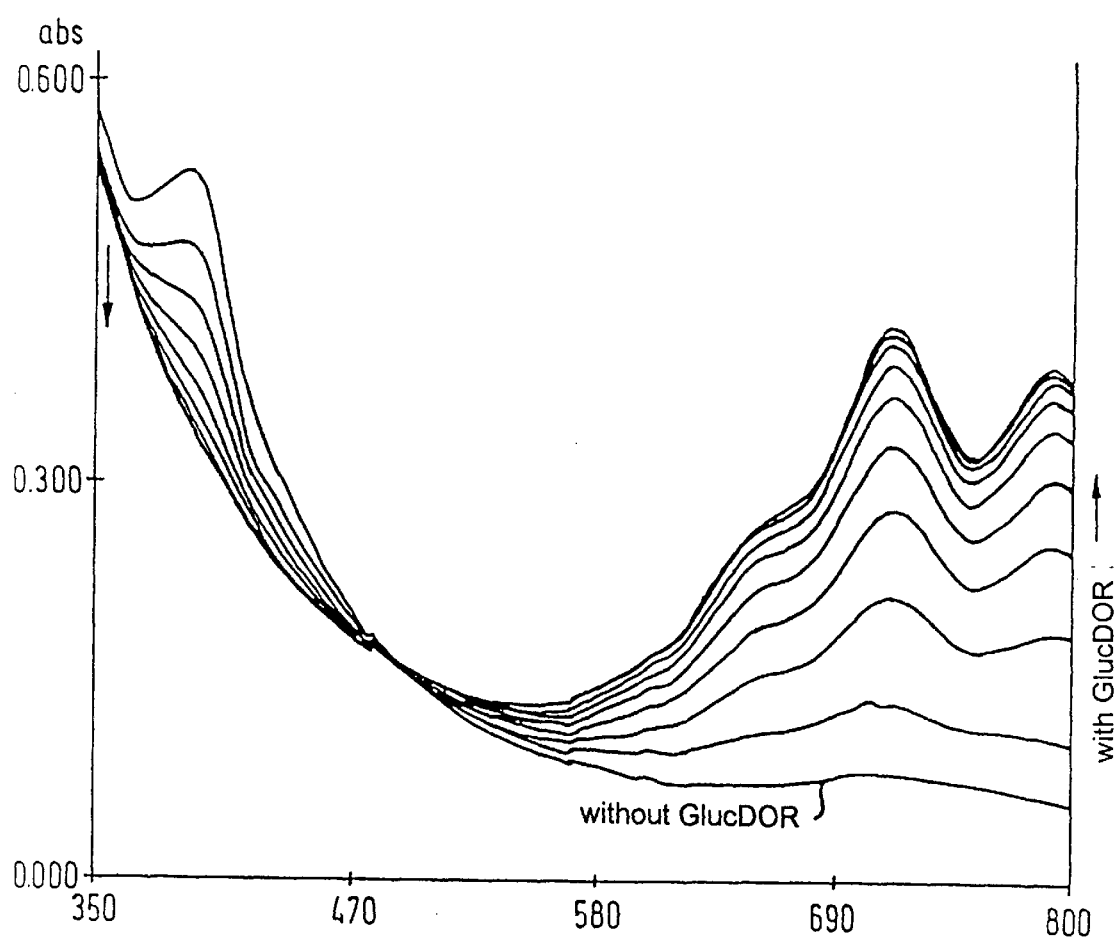
FIG. 5 shows UV/Vis spectra of an indicator according to the invention for the detection of glucose.

The following are mixed in a cuvette:
20 μl of a 5 mM solution of the indicator (dehydroindanthrone disulfonic acid disodium salt) in distilled water
1870 μl 0.1 M phosphate buffer pH=7
10 μl 1 M glucose solution
100 μl of a GlucDOR solution (in 0.05 M Hepes buffer pH 7.0 containing PQQ c=0.016 mg/ml and calcium chloride c=0.7 mol/l) at a concentration of 300 U/ml is added. A UV/Vis spectrum is recorded every 60 sec. after addition (FIG. 5). No further colour change can be measured after 8 min.

Example 9

Figure 6:
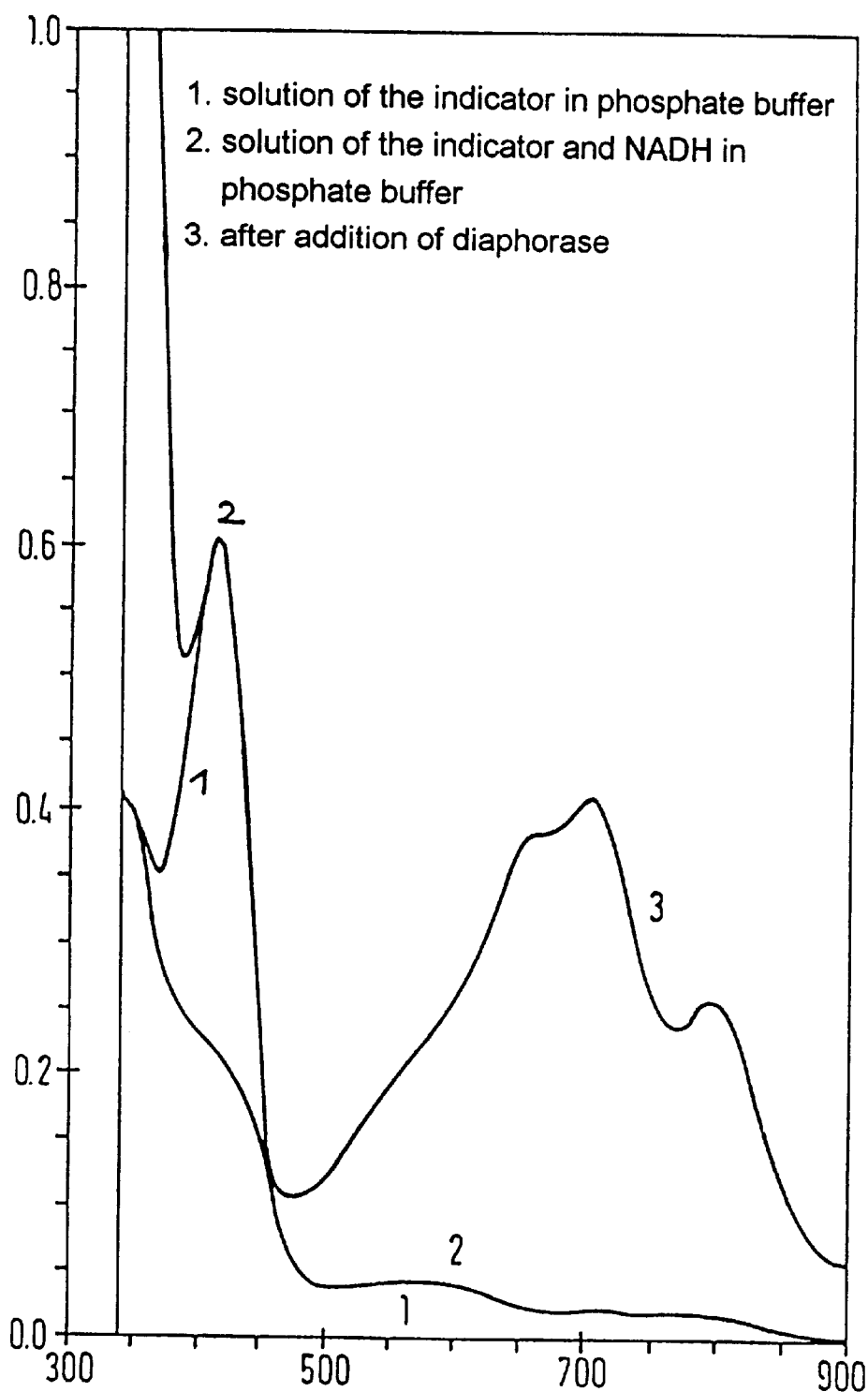
FIG. 6 shows UV/Vis spectra of an indicator according to the invention for the detection of NADH in the presence of the mediator diaphorase.

Reaction of an indicator with NADH/diaphorase
The following are mixed in a cuvette:
20 μl of a 5 mM solution of the 8,13-dihydrobenzo[a]naphtho[2,3-h]phenazine-8,13-dione-3,6-disulfonic acid disodium salt or of the[2,3-j]-isomer in distilled water
1870 μl 0.1 M phosphate buffer pH=7
10 μl of a 0.1 M NADH solution in distilled water
100 μl of a diaphorase solution dissolved in 0.1 M phosphate buffer pH=7 at a concentration of 100 U/ml is added to this and a UV/Vis spectrum is recorded after 60 sec. (FIG. 6).

Example 10

Figure 7:
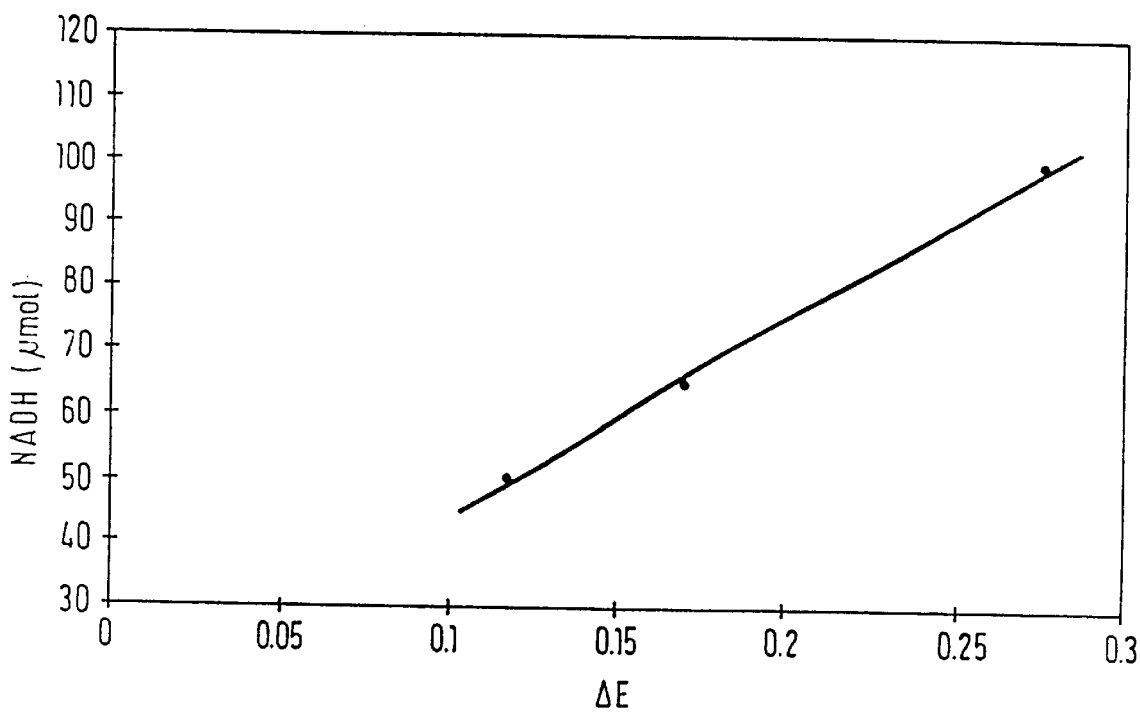
FIG. 7 shows a UV/Vis spectrum of the determination of NADH with an indicator according to the invention in the presence of the mediator diaphorase.

Determination of NADH
Measurement mixture: (final concentrations)
phosphate buffer pH=7 100 mM
indicator: 0.5 mM
(8,13-dihydro-benzo[a]naphtho[2,3-h]phenazine-8,13-dione-3,6-disulfonic acid disodium salt) or the [2,3-j]-isomer
NADH: 50–100 μmol
A final concentration in the cuvette of 5 U/ml is adjusted with a diaphorase solution (100 U/ml, 0.1 M phosphate buffer pH=7) and the change in absorbance at 704 nm is determined after one minute. An increasing amount of a glue-green dye is formed with increasing NADH concentrations (FIG. 7).

Example 11

Kinetics of the reaction of an indicator with phenazine methosulfate/NADH
The following are mixed successively in a cuvette:
20 μl of a 5 mM solution of 8,13-dihydro-benzo[a]naphtho[2,3-h]phenazine-8,13-dione-3,6-disulfonic acid disodium salt in distilled water
1870 μl 0.1 M phosphate buffer pH=7
10 μl of a 0.1 M NADH solution in distilled water
100 μl of a phenazine methosulfate solution dissolved in distilled water at a concentration of 10 μg/ml.

Figure 8:
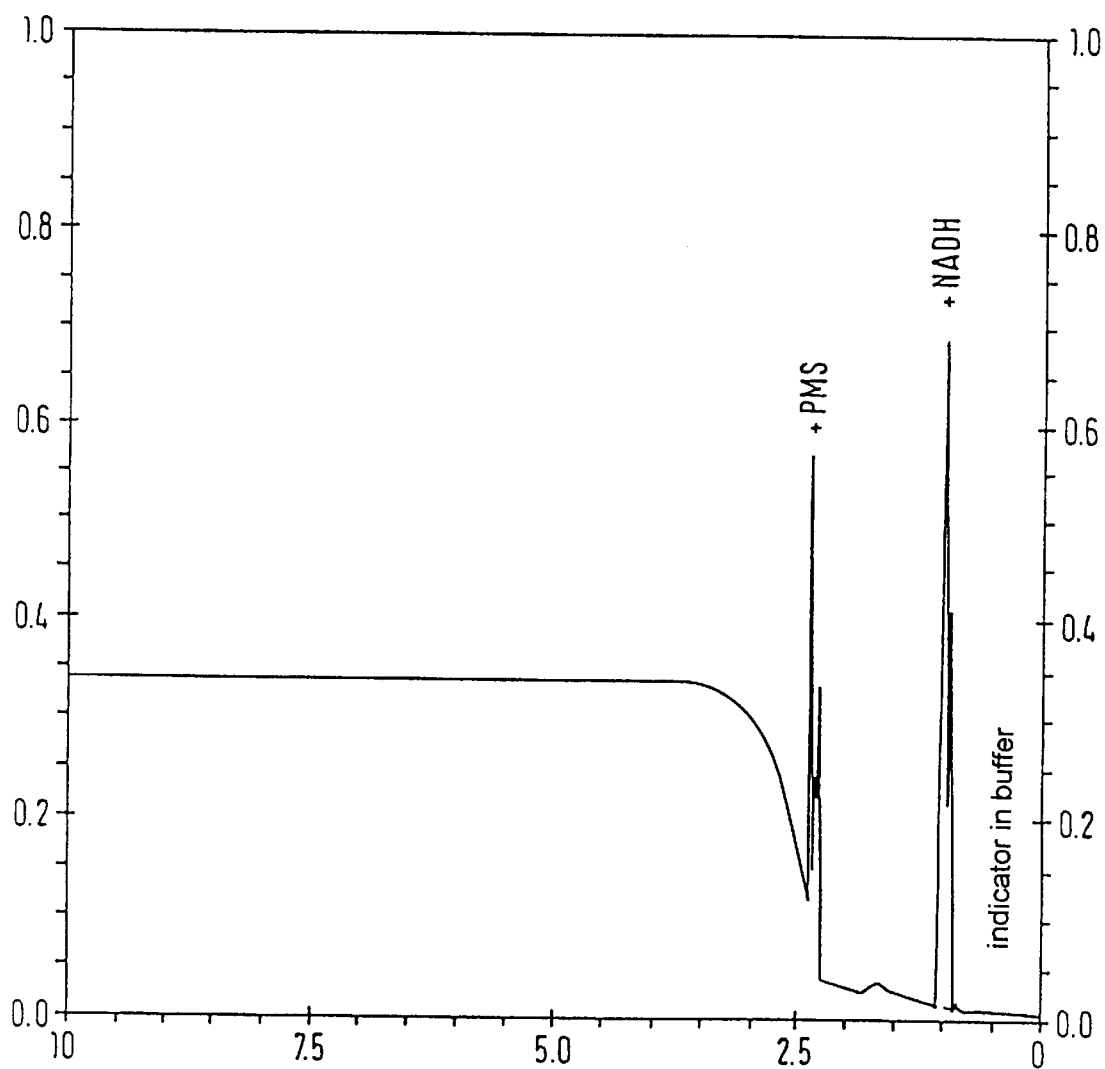
FIG. 8 shows a UV/Vis spectrum of the kinetics of the reaction of an indicator according to the invention with NADH in the presence of the mediator phenazine methosulfate.

The absorbance at 703 nm is measured in relation to time (see FIG. 8). The blue dye is formed after adding the mediator.

Example 12:

Combination with a hydrolase substrate

The following are placed in a cuvette:

20 μl of a 5 mM solution of 3-indolyl-β-D-galactopyranoside

1860 μl 0.1 M phosphate buffer pH=7 A UV/Vis spectrum is recorded.

Then 100 μl of a β-galactosidase solution in 0.1 M phosphate buffer pH=7 (384 U/ml) is added. 150 sec. after the addition a UV/Vis spectrum is recorded. The absorption bands of the indigo formed by atmospheric oxygen can be weakly seen.

Figure 9:
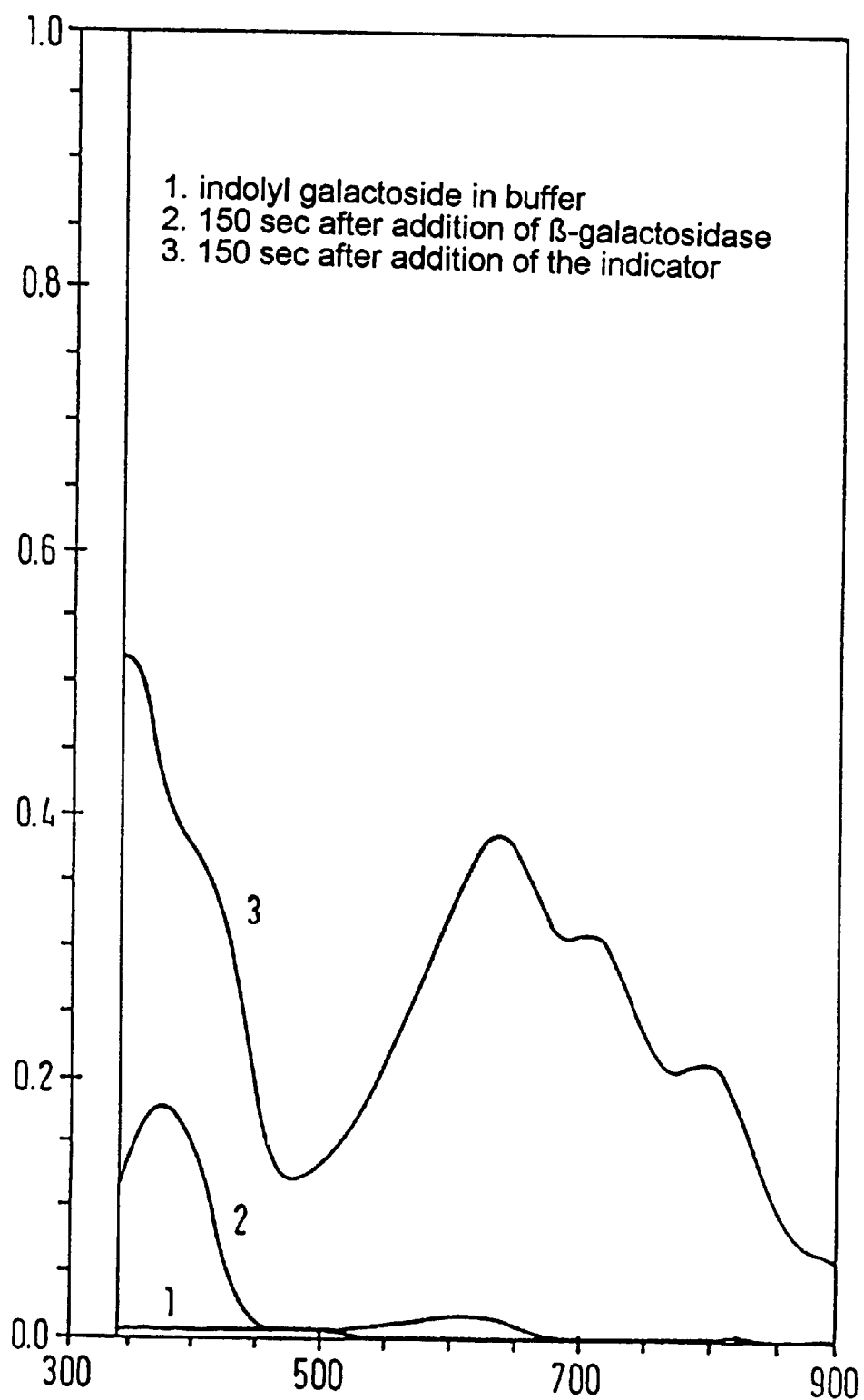
FIG. 9 shows a UV/Vis spectrum of an indicator according to the invention in a determination of β-galactosidase activity.

Then 20 μl of a 5 mM solution of 8,13-dihydro-benzo[a]-naphtho[2,3-h]phenazine-8,13-dione-3,6-disulfonic acid disodium salt or the [2,3-j]-isomer in distilled water is added. A UV/Vis spectrum is recorded after 150 sec. A deep-blue solution is formed. The absorption bands of both dyes can be seen (see FIG. 9).

Example 13

Light stability of commercial NBT (4-nitro blue tetrazolium chloride, Boehringer Mannheim GmbH 1 087 479 Ch 14528121) and the 8,13-dihydro-benzo[a]-naphtho[2,3-h]phenazine-8,13-dione-3,6-disulfonic acid disodium salt or the [2,3-j]-isomer in a standard buffer of the Boehringer Mannheim Test kit (order No. 1101 668) for the determination of fructose with NBT (J. D. Kruse-Jarres, J. Jarausch et al. Laboratoriumsmedizin 1989, 13, 245)

Figure 10A:
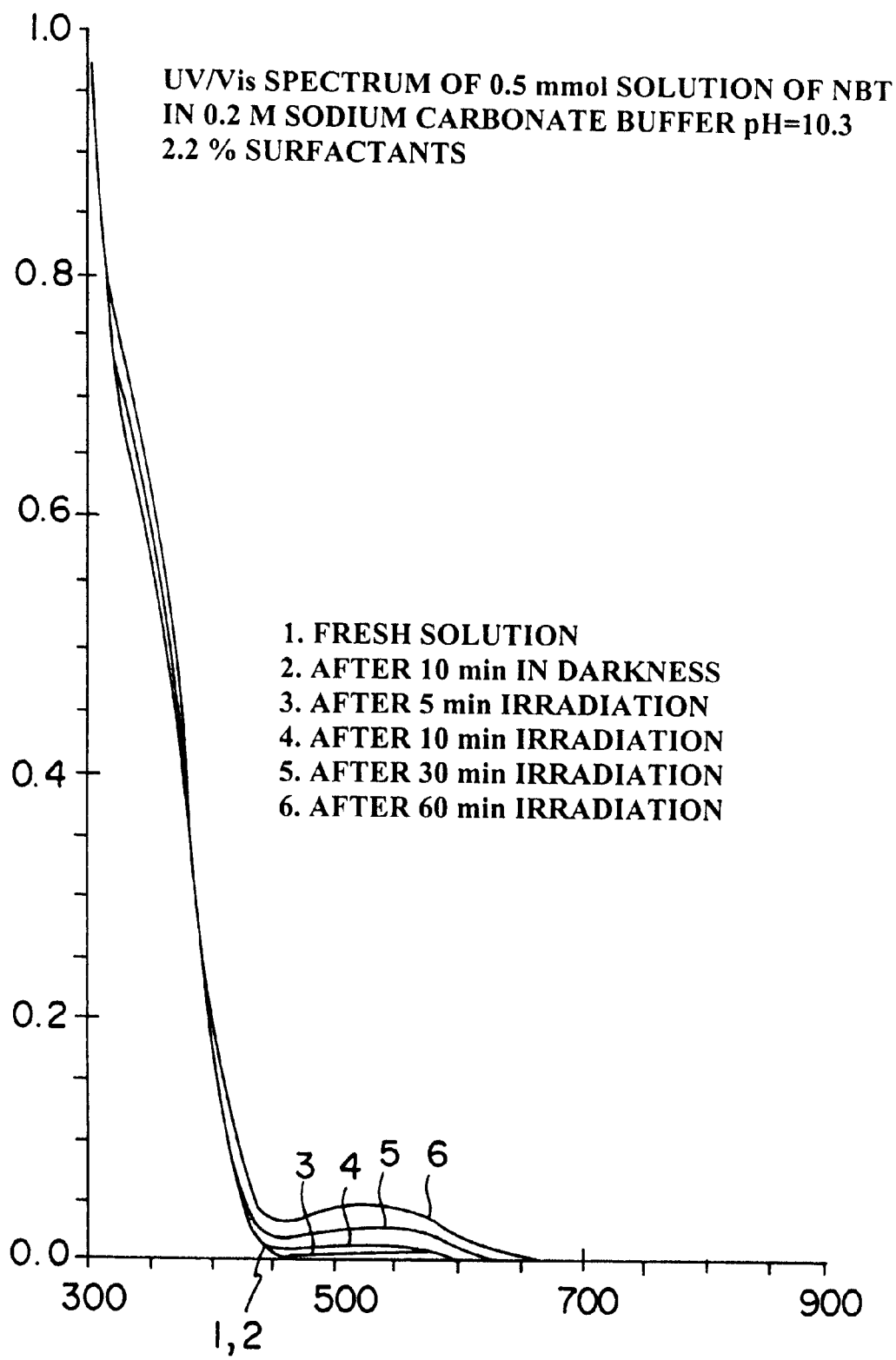
FIG. 10 shows a comparison of the light stability of a tetrazolium salt with that of an indicator according to the invention.
Figure 10B:
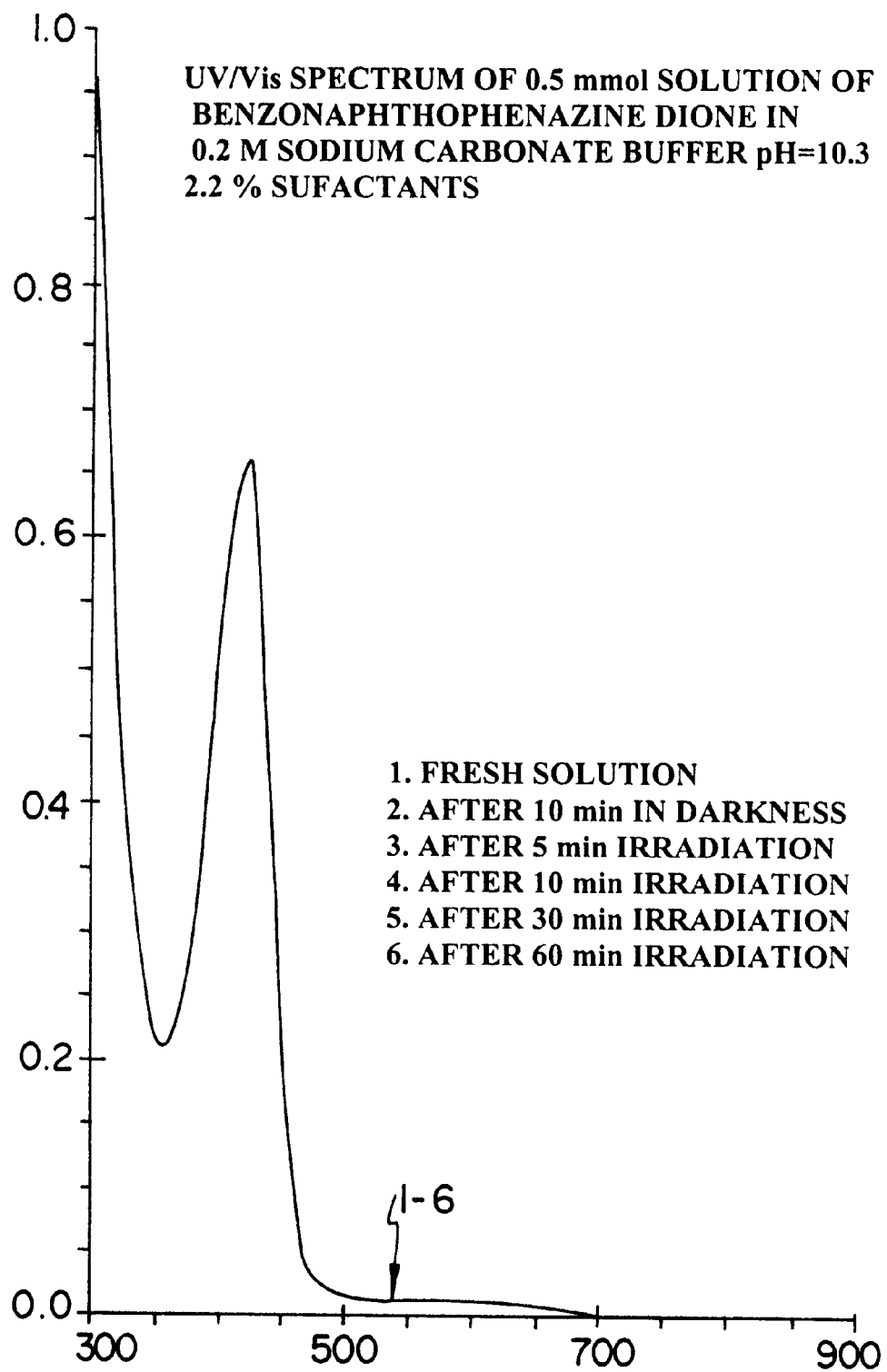

0.5 mM solutions of NBT or of the benzonaphthophenazinedione in a 0.2 M sodium carbonate buffer pH=10.3 containing 2.2% surfactants are freshly prepared. A UV/Vis spectrum is recorded. A further spectrum is recorded after allowing it to stand for 10 min in the dark at room temperature. The spectra do not change. Subsequently it is irradiated with a 60 W krypton lamp: distance from the radiation source 30 cm, room temperature. Spectra are recorded after 5, 10, 30, 60 min. total irradiation time. In the case of the NBT solution the UV/Vis spectrum changes with increasing irradiation time. A violet colouration can be observed visually. In contrast the benzonaphthophenazine-dione solution does not change (see FIG. 10).

We claim:

1. In a method for the quantitative or qualitative detection of an analyte in a sample comprising contacting the sample with a reagent having a detectable property and quantitatively or qualitatively detecting the analyte by detecting a change in the detectable property of the reagent, the improvement wherein the reagent comprises a compound of formula I and/or formula II

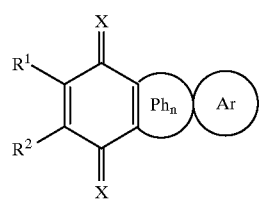
(I)

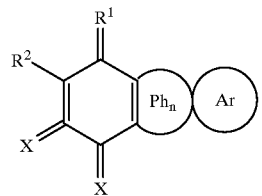
(II)

wherein $R^1$ and $R^2$ are each independently hydrogen, halogen or an organic residue, or together form a substituted or unsubstituted aromatic or heteroaromatic ring system, X is O, S, C(Acc)$_2$, CH(Acc) or N(Acc), wherein Acc is an electron-attracting group, Ph is a phenyl ring which is unsubstituted or substituted, n is 0 to 4, and Ar is a group of formula IIIa, IIIb, IVa, IVb, Va, Vb, VIa or VIb:

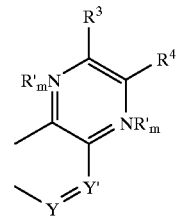
(IIIa)

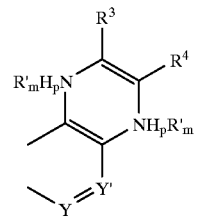
(IIIb)

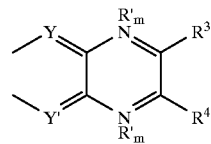
(IVa)

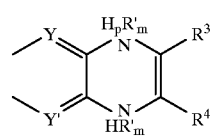
(IVb)

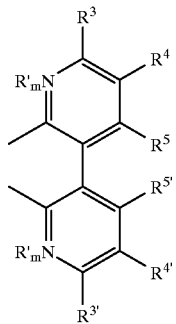

(Va)

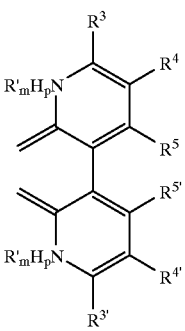

(Vb)

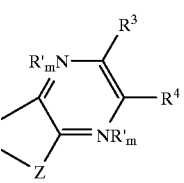

(VIa)

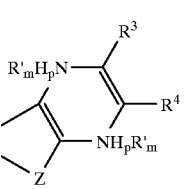

(VIb)

wherein

R³, R³', R⁴, R⁴', R⁵ and R⁵' are each independently hydrogen, halogen or an organic residue, or (a) R³ and R⁴ and/or R³' and R⁴' or (b) R⁴ and R⁵ and/or R⁴' and R⁵' in each case together form a ring system comprising an aromatic or heteroaromatic ring, Y and Y' are each independently N or CR⁶, wherein R⁶ is hydrogen, halogen or an organic residue, Z is NR, O or S, wherein R is hydrogen or an organic residue, R' is in each case independently a substituted or unsubstituted alkyl or aryl residue, and m is in each case independently 0 or 1, wherein when m is 1 then a nitrogen bound to R' in the formulae IIIa, IVa, Va and VIa carries a positive charge and a counterion is present, and p is 0 in the formulae IIIb, IVb, Vb and VIb, and wherein m is 0 then p is 1.

2. The method of claim 1, wherein the method comprises causing a redox reaction to occur, wherein the reagent participates in the redox reaction, and thereafter detecting a change in the detectable property of the reagent due to the redox reaction.

3. The method of claim 2, wherein the change is detected spectroscopically.

4. The method of claim 3, wherein the change is in the absorption or fluorescence property of the reagent.

5. The method of claim 2, wherein the change is in the electrochemical property of the reagent.

6. The method of claim 1, wherein the analyte is detected directly via the change in the detectable property of the reagent.

7. The method of claim 1, wherein the analyte is detected via the change in the detectable property of the reagent, coupled with a further detection system.

8. The method of claim 1, wherein the analyte is an oxidoreductase or an oxidoreductase substrate and the detecting step comprises determining any oxidoreductase activity.

9. The method of claim 8, wherein the method further comprises contacting the sample with an oxidoreductase co-substrate.

10. The method of claim 9, wherein the oxidoreductase co-substrate is NAD(P)⁺, NAD(P)H/H⁺ or PQQ.

11. The method of claim 9, wherein the oxidoreductase activity is determined in the presence of mediators which catalyze the transfer of electrons from the oxidoreductase co-substrate onto an oxidized compound or the transfer of electrons from a reduced compound onto the oxidoreductase co-substrate.

12. The method of claim 8, wherein the analyte is glucose.

13. The method of claim 1, wherein the analyte is a hydrolase or a hydrolase substrate and the detecting step comprises determining any hydrolase activity.

14. The method of claim 13, wherein the hydrolase is a lipase, β-galactosidase or alkaline phosphatase.

15. The method of claim 13, wherein the hydrolase activity is determined using an oxidative coupling system in which the hydrolase substrate is cleaved to produce an oxidizable compound and the oxidizable compound is reduced.

16. The method of claim 1, wherein at least one of R¹ and R² comprises a substituted or unsubstituted aromatic or heteroaromatic ring system.

17. The method of claim 1, wherein R¹ and R² together form a substituted or unsubstituted aromatic or heteroaromatic ring system.

18. The method of claim 17, wherein R¹ and R² together form a substituted or unsubstituted benzene ring.

19. The method of claim 1, wherein at least one of R³, R³', R⁴, R⁴', R⁵ and R⁵' comprises a substituted or unsubstituted aromatic or heteroaromatic ring system.

20. The method of claim 1, wherein R³ and R⁴ together form a ring system comprising an aromatic or heteroaromatic ring.

21. The method of claim 1, wherein (a) R³ and R⁴ and/or R³' and R⁴' or (b) R⁴ and R⁵ and/or R⁴' and R⁵' in each case together form a ring system comprising an aromatic or heteroaromatic ring.

22. The method of claim 21, wherein (a) R³ and R⁴ and/or R³' and R⁴' or (b) R⁴ and R⁵ and/or R⁴' and R⁵' in each case together form a substituted or unsubstituted naphthalene or anthraquinone ring system.

23. The method of claim 1, wherein the compound contains at least one hydrophilic group.

24. The method of claim 23, wherein the hydrophilic group is selected from the group consisting of (a) carboxylic acid, sulfonic acid and phosphonic acid groups, or salts thereof, (b) sulfuric acid monoester, phosphoric acid monoester and phosphoric acid diester groups, or salts thereof, (c) primary, secondary or tertiary amine groups and quarternary ammonium groups, (d) polyhydroxy groups, (e) $C_2$–$C_3$ polyalkylenethio groups and (f) groups which contain a combination of two or more of the groups (a)–(e).

25. The method of claim 1, wherein the compounds are used in the form of metal complexes.

26. A reagent for the determination of an analyte, comprising at least one compound of formula I and/or formula II

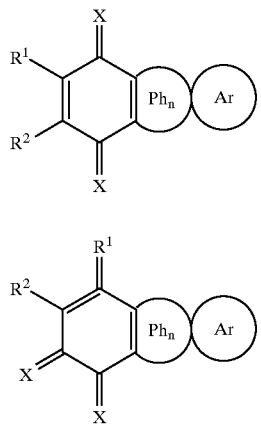

(I)

(II)

wherein $R^1$ and $R^2$ are each independently hydrogen, halogen or an organic residue, or together form a substituted or unsubstituted aromatic or heteroaromatic ring system, X is O, S, C(Acc)$_2$, CH(Acc) or N(Acc), wherein Acc is an electron-attracting group, Ph is a phenyl ring which is unsubstituted or substituted, n is 0 to 4, and Ar is a group of formula IIIa, IIIb, IVa, IVb, Va, Vb, VIa or VIb:

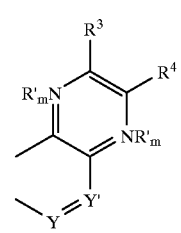

(IIIa)

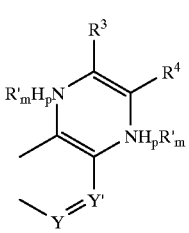

(IIIb)

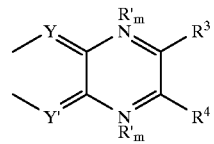

(IVa)

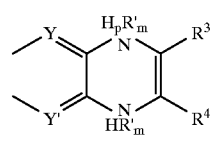

(IVb)

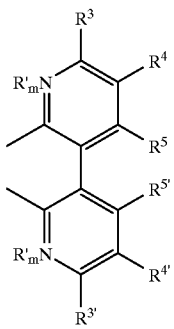

(Va)

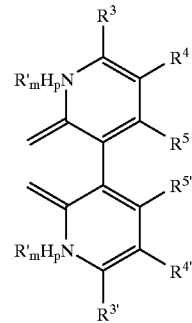

(Vb)

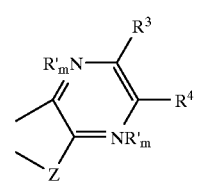

(VIa)

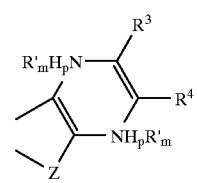

(VIb)

wherein $R^3$, $R^{3'}$, $R^4$, $R^{4'}$, $R^5$ and $R^{5'}$ are each independently hydrogen, halogen or an organic residue, or (a) $R^3$ and $R^4$ and/or $R^{3'}$ and $R^{4'}$ or (b) $R^4$ and $R^5$ and/or $R^{4'}$ and $R^{5'}$ in each case together form a ring system comprising an aromatic or heteroaromatic ring, Y and Y' are each independently N or CR$^6$, wherein R$^6$ is hydrogen, halogen or an organic residue, Z is NR, O or S, wherein R is hydrogen or an organic residue, R' is in each case independently a substituted or unsubstituted alkyl or aryl residue, and m is in each case independently 0 or 1, wherein when m is 1 then a nitrogen bound to R' in the formulae IIIa, IVa, Va and VIa carries a positive charge and a counterion is present, and p is 0 in the formulae IIIb, IVb, Vb and VIb, and wherein m is 0 then p is 1.

27. The reagent of claim 26, wherein the reagent is present in a solution or suspension in an aqueous or non-aqueous liquid, or as a powder or lyophilisate.

28. The reagent of claim 26, wherein the reagent is present absorbed into an absorptive or swellable carrier or incorporated into a light-sensitive film layer.

29. A reagent kit, containing a reagent as claimed in claim 26 and additional test components.

30. The reagent kit of claim 29, wherein the additional test components modify the detectable property of the at least one compound.

31. A compound of formula I or formula II

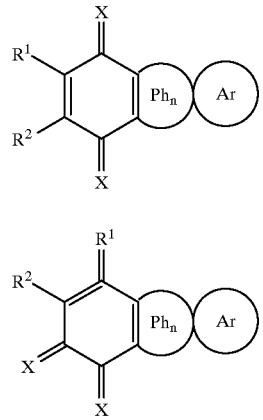

(I)

(II)

wherein

R$^1$ and R$^2$ are each independently hydrogen, halogen or an organic residue, or together form a substituted or unsubstituted aromatic or heteroaromatic ring system, X is O, S, C(Acc)$_2$, CH(Acc) or N(Acc), wherein Acc is an electron-attracting group, Ph is a phenyl ring which is unsubstituted or substituted, n is 0 to 4, and Ar is a group of formula IIIa, IIIb, IVa, IVb, Va, Vb, VIa or VIb:

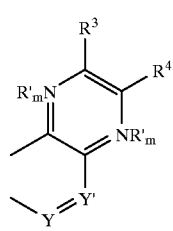

(IIIa)

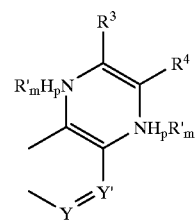

(IIIb)

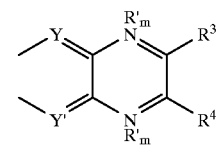

(IVa)

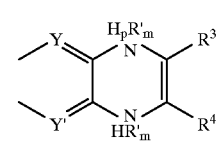

(IVb)

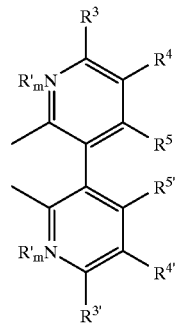

(Va)

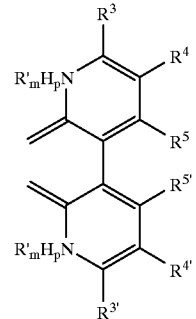

(Vb)

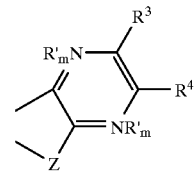

(VIa)

-continued

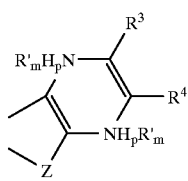

(VIb)

wherein
- $R^3$, $R^{3'}$, $R^4$, $R^{4'}$, $R^5$ and $R^{5'}$ are each independently hydrogen, halogen or an organic residue, or (a) $R^3$ and $R^4$ and/or $R^{3'}$ and $R^{4'}$ or (b) $R^4$ and $R^5$ and/or $R^{4'}$ and $R^{5'}$ in each case together form a ring system comprising an aromatic or heteroaromatic ring,
- Y and Y' are each independently N or $CR^6$, wherein $R^6$ is hydrogen, halogen or an organic residue,
- Z is NR, O or S, wherein R is hydrogen or an organic residue,
- R' is in each case independently a substituted or unsubstituted alkyl or aryl residue, and
- m is in each case independently 0 or 1, wherein when m is 1 then a nitrogen bound to R' in the formulae IIIa, IVa, Va and VIa carries a positive charge and a counterion is present, and p is 0 in the formulae IIIb, IVb, Vb and VIb, and wherein m is 0 then p is 1,
- wherein the compound contains at least one hydrophilic group except indanthrene monosulfonic acid, indanthrene disulfonic acid and sodium or potassium salts thereof.

32. The compound of claim 31, wherein the compound has the formula VIIa or VIIb

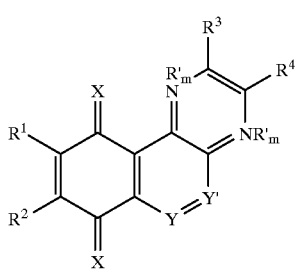

(VIIa)

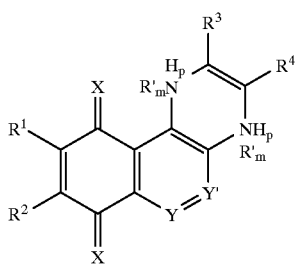

(VIIb)

wherein $R^1$, $R^2$, X, R', m, p, $R^3$, $R^4$, Y and Y' are as defined above.

33. The compound of claim 31, wherein the compound has the formula VIIIa or VIIIb

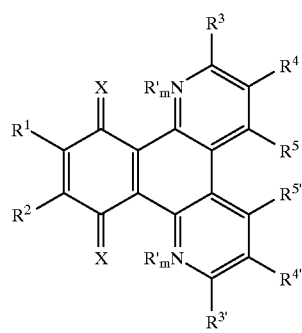

(VIIIa)

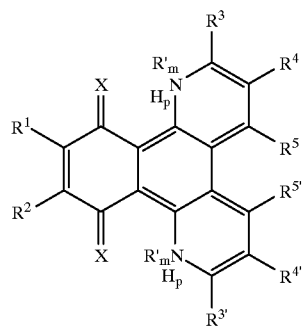

(VIIIb)

wherein $R^1$, $R^2$, X, R', m, p, $R^3$, $R^4$, $R^5$, $R^{3'}$, $R^{4'}$ and $R^{5'}$ are as defined above.

34. The compound of claim 31, wherein X is O.

35. The compound of claim 31, wherein at least one of $R^1$ and $R^2$ comprises a substituted or unsubstituted aromatic or heteroaromatic ring system.

36. The compound of claim 32, wherein at least one of $R^3$ and $R^4$ comprises a substituted or unsubstituted aromatic or heteroaromatic ring system.

37. The compound of claim 32, wherein Y and Y' each are $CR^6$, wherein $R^6$ is as stated above.

38. The compound of claim 33, wherein at least one of $R^3$, $R^4$, $R^5$, $R^{3'}$, $R^{4'}$ and $R^{5'}$ comprises a substituted or unsubstituted aromatic or heteroaromatic ring system.

39. The method of claim 8, wherein any dye-oxidoreductase activity is determined.

40. The method of claim 8, wherein any glucose-dye-oxidoreductase activity is determined.

* * * * *